United States Patent
Hagerlid et al.

(10) Patent No.: US 7,427,379 B1
(45) Date of Patent: Sep. 23, 2008

(54) LIQUID DISPENSING APPARATUS

(75) Inventors: Peter Hagerlid, Uppsala (SE); Hanno Ehring, Uppsala (SE); Björn Ekström, Uppsala (SE)

(73) Assignee: Biotage AB, Uppsala (SE)

( * ) Notice: Subject to any disclaimer, the term of this patent is extended or adjusted under 35 U.S.C. 154(b) by 0 days.

(21) Appl. No.: 09/936,932

(22) PCT Filed: Mar. 20, 2000

(86) PCT No.: PCT/GB00/01029

§ 371 (c)(1),
(2), (4) Date: Jan. 16, 2002

(87) PCT Pub. No.: WO00/56455

PCT Pub. Date: Sep. 28, 2000

(30) Foreign Application Priority Data

Mar. 19, 1999 (GB) .................................. 9906477.6

(51) Int. Cl.
*B01L 3/02* (2006.01)
*G01N 1/14* (2006.01)

(52) U.S. Cl. .................. 422/100; 422/101; 422/102; 73/863.32; 73/863.31; 73/863.81; 73/863.83; 73/863.85; 73/864; 73/864.01; 73/864.03; 73/864.11; 73/864.14

(58) Field of Classification Search ........... 422/99–102, 422/68.1; 73/863.32, 863.25, 863.31, 863.81, 73/863.83, 863.85, 864, 864.01, 864.03, 73/864.11, 864.12, 864.14
See application file for complete search history.

(56) References Cited

U.S. PATENT DOCUMENTS

| | | | |
|---|---|---|---|
| 3,572,552 A * | 3/1971 | Guinn ........................ 222/263 |
| 4,058,370 A * | 11/1977 | Suovaniemi ................. 422/100 |
| 4,087,248 A * | 5/1978 | Miles .......................... 436/506 |
| 4,106,911 A * | 8/1978 | Marcelli ....................... 422/63 |
| 4,444,062 A * | 4/1984 | Bennett et al. ........... 73/863.32 |
| 4,734,262 A * | 3/1988 | Bagshawe ................... 422/101 |
| 4,895,706 A * | 1/1990 | Root et al. .................. 422/102 |
| 4,902,481 A * | 2/1990 | Clark et al. ................. 422/101 |
| 4,948,564 A * | 8/1990 | Root et al. .................. 422/101 |
| 4,952,516 A * | 8/1990 | Matkovich .................. 436/170 |
| 5,010,930 A | 4/1991 | Columbus ..................... 141/1 |
| 5,035,866 A * | 7/1991 | Wannlund .................... 422/102 |
| 5,055,263 A * | 10/1991 | Meltzer ........................ 422/65 |
| 5,171,538 A * | 12/1992 | Tremmel et al. ............ 422/100 |

(Continued)

FOREIGN PATENT DOCUMENTS

EP 0 048 917 B1 4/1982

(Continued)

*Primary Examiner*—Brian R. Gordon
(74) *Attorney, Agent, or Firm*—Dorsey & Whitney LLP

(57) ABSTRACT

A liquid dispensing apparatus comprises a liquid reservoir (32), an outlet port (6; 36) and driving means for forcing liquid (4) through the outlet port (6, 36). The driving means generates a pulse of gas which impinges upon the liquid (4) in the reservoir (32) so as to force liquid (4) through the outlet port (6, 36). Also disclosed is a cassette comprising a plurality of cartridges for dispensing liquid therefrom. Each cartridge comprises a liquid reservoir (32) and an outlet member (36) mounted so as to close an opening (34) in the liquid reservoir (32). The outlet member (36) provides an outlet port through which the liquid can be forced by a pulse of pressurised gas.

15 Claims, 2 Drawing Sheets

U.S. PATENT DOCUMENTS

| | | | |
|---|---|---|---|
| 5,356,814 A * | 10/1994 | Carrico et al. | 435/283.1 |
| 5,435,462 A * | 7/1995 | Fujii | 222/82 |
| 5,496,523 A * | 3/1996 | Gazit et al. | 422/100 |
| 5,497,670 A * | 3/1996 | Carl | 73/863.32 |
| 5,603,899 A * | 2/1997 | Franciskovich et al. | 422/100 |
| 5,736,105 A * | 4/1998 | Astle | 422/100 |
| 5,746,975 A * | 5/1998 | Chateau | 422/61 |
| 5,789,251 A * | 8/1998 | Astle | 436/48 |
| 5,846,493 A * | 12/1998 | Bankier et al. | 422/101 |
| 5,888,831 A * | 3/1999 | Gautsch | 436/177 |
| 6,024,925 A * | 2/2000 | Little et al. | 422/100 |
| 6,027,694 A * | 2/2000 | Boulton et al. | 422/102 |
| 6,149,872 A * | 11/2000 | Mack et al. | 422/100 |
| 6,200,533 B1 * | 3/2001 | Blevins et al. | 422/102 |
| 6,296,811 B1 * | 10/2001 | Sasaki | 422/100 |
| 6,309,605 B1 * | 10/2001 | Zermani | 422/101 |
| 6,376,256 B1 * | 4/2002 | Dunnington et al. | 506/30 |
| 6,401,552 B1 * | 6/2002 | Elkins | 73/863 |
| 6,464,942 B2 * | 10/2002 | Coffman et al. | 422/100 |
| 6,489,132 B1 * | 12/2002 | Gordon et al. | 435/7.92 |
| 6,491,873 B2 * | 12/2002 | Roberts et al. | 422/101 |
| 6,500,390 B1 * | 12/2002 | Boulton et al. | 422/100 |
| 6,534,019 B1 * | 3/2003 | Inoue | 422/130 |
| 6,551,557 B1 * | 4/2003 | Rose et al. | 422/100 |
| 6,566,145 B2 * | 5/2003 | Brewer | 436/178 |
| 6,569,385 B1 * | 5/2003 | Little et al. | 422/100 |
| 6,706,538 B1 * | 3/2004 | Karg et al. | 436/180 |
| 6,783,732 B2 * | 8/2004 | Madden et al. | 422/63 |
| 6,824,024 B2 * | 11/2004 | Ingenhoven et al. | 222/504 |
| 6,841,130 B2 * | 1/2005 | Lehtinen et al. | 422/100 |
| 6,852,290 B2 * | 2/2005 | Hager et al. | 422/101 |
| 6,869,571 B2 * | 3/2005 | Ingenhoven et al. | 422/100 |
| 6,969,489 B2 * | 11/2005 | Freeman | 422/100 |
| 2001/0016177 A1 * | 8/2001 | Pelc et al. | 422/100 |
| 2001/0055814 A1 * | 12/2001 | Sasaki | 436/180 |
| 2002/0012611 A1 * | 1/2002 | Stylli et al. | 422/65 |
| 2002/0159918 A1 * | 10/2002 | Tseng et al. | 422/100 |
| 2002/0159919 A1 * | 10/2002 | Churchill et al. | 422/100 |
| 2003/0026732 A1 * | 2/2003 | Gordon et al. | 422/63 |
| 2003/0207464 A1 * | 11/2003 | Lemmo et al. | 436/180 |
| 2004/0115098 A1 * | 6/2004 | Kearney et al. | 422/102 |
| 2004/0147042 A1 * | 7/2004 | Gratzl et al. | 436/180 |
| 2004/0166028 A1 * | 8/2004 | Husar et al. | 422/100 |
| 2004/0202581 A1 * | 10/2004 | Berndt | 422/100 |
| 2005/0271551 A1 * | 12/2005 | Shumate et al. | 422/100 |
| 2006/0039823 A1 * | 2/2006 | Yamakawa et al. | 422/63 |
| 2007/0041876 A1 * | 2/2007 | Legge | 422/100 |

FOREIGN PATENT DOCUMENTS

| | | |
|---|---|---|
| EP | 0 351 995 B1 | 1/1990 |
| EP | 0 434 149 A2 | 6/1991 |
| EP | 0 502 564 B1 | 9/1992 |
| EP | 0941854 | 9/1999 |
| GB | 1 380 350 | 1/1975 |
| GB | 1 437 738 | 6/1976 |
| GB | 1 455 664 | 11/1976 |
| GB | 1 497 012 | 1/1978 |
| WO | WO97/15394 | 5/1997 |
| WO | WO98/20020 | 5/1998 |
| WO | WO98/29736 | 7/1998 |
| WO | WO99/36176 | 7/1999 |
| WO | WO99/42805 | 8/1999 |

* cited by examiner

LIQUID DISPENSING APPARATUS

BACKGROUND OF THE INVENTION

This invention relates to liquid dispensing apparatus and in particular to liquid dispensing apparatus which are able to dispense small volumes of liquid.

In certain applications it is desirable to be able to dispense very small volumes of liquid from a container, for example in the range 10-500 nanoliters (nl). Drops of this size cannot normally be produced by pumping liquid out of a capillary since surface tension will hold the drop to the tip of the capillary until it is sufficiently large that its weight overcomes this surface tension. This does not happen until the volume of the drop is of the order of 10 to 50 microliters—i.e. 2 to 3 orders of magnitude greater than the range of interest.

Devices are available which overcome this limitation by forcing a measured amount of liquid through the tip of a nozzle using a piezo-electric actuator acting on the liquid. However such systems are expensive and may only be used with a single type of liquid at a time—thus multiplying the cost where several different liquids need to be dispensed.

BRIEF SUMMARY OF THE INVENTION

It is an object of the present invention to provide an improved apparatus and when viewed from a first aspect the invention provides a liquid dispensing apparatus comprising a liquid reservoir, an outlet port and driving means for forcing liquid through said outlet port, said driving means comprising means for generating a pulse of gas which impinges upon liquid in the reservoir so as to force liquid through the outlet port.

Thus it will be seen that in accordance with the invention liquid may be dispensed by forcing it through the outlet port by means of a pulse of gas. The volume of liquid dispensed may be controlled by adjusting the amplitude and duration of the gas pulse. It has been found that this enables accurate control of the volume dispersed, down to the order of 50-500 nl in the preferred embodiment. Furthermore as a gas is used as the medium for transmitting force to the liquid, it is not necessary for any part of the driving means to be in contact with the liquid to be dispensed. This has clear advantages both from the point of view of preventing contamination of the liquid and also the reduced necessity to clean the apparatus.

As the driving impulse is applied to liquid in the reservoir, it is not necessary to have any part of the driving means arranged in the vicinity of the outlet port. This means that the outlet port can be simple to manufacture and the outlet port may even be provided on a disposable member.

DETAILED DESCRIPTION OF THE INVENTION

Figure 1:
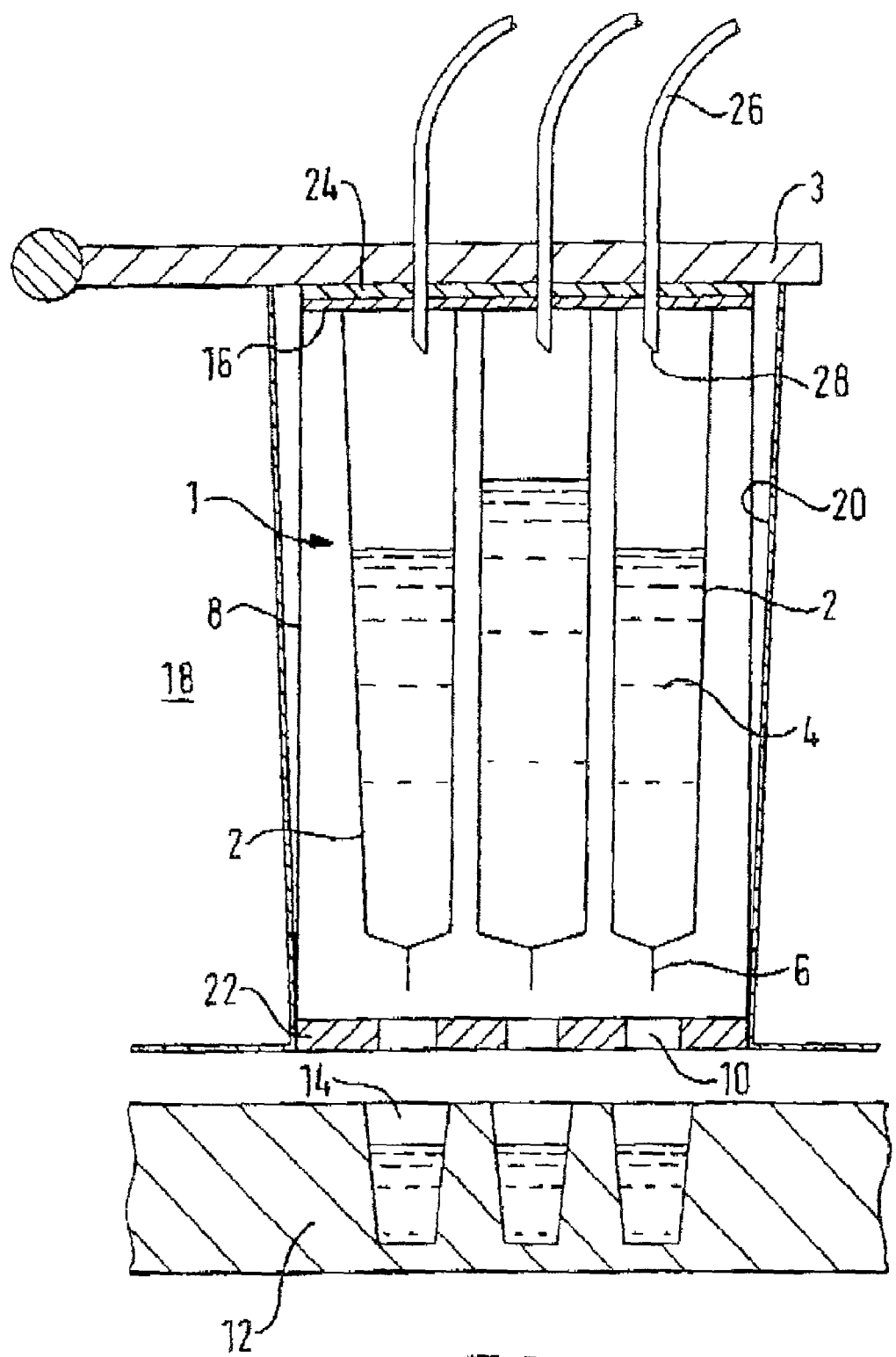
FIG. 1 is a schematic view of a cassette of cartridges and liquid dispensing apparatus in accordance with the invention.

In one preferred arrangement in accordance with the invention, the outlet port is an integral part of the apparatus. In a particularly preferred embodiment one or both of the outlet port and the liquid reservoir are moulded from a suitable plastics material, thereby allowing them to be made disposable. More preferably the outlet port and liquid reservoir are both moulded from suitable plastics, most preferably integrally with each other, to form a cartridge. Alternatively such a cartridge could be made from one or more other suitable materials such as silica or stainless steel.

Cartridges of the kind described above may be provided singly, but preferably a plurality are provided in a cassette. Such an arrangement is novel and advantageous in itself and thus when viewed from a second aspect the present invention provides a cassette comprising a plurality of cartridges for dispensing liquid therefrom, each cartridge comprising an outlet port in the form of a protruding nozzle and a liquid reservoir integrally formed therewith.

Preferably the cartridges are formed integrally with one another to form said cassette.

The invention makes it possible, at least in some preferred embodiments, to provide cartridges pre-filled with the necessary liquid and having the required outlet port formed integrally therewith. All that is necessary then is simply to place the liquid reservoir of the cartridge or each cartridge of a cassette of cartridges in gaseous communication with a means to generate gas pulses, in order to form a liquid dispensing apparatus in accordance with the first aspect of the invention. This is extremely convenient to a user who thus does not need to be concerned with filling reservoirs with liquid, cleaning the outlet port etc. Indeed in at least preferred embodiments of this aspect of the invention, contact with the liquid to be dispensed may be completely avoided.

In other preferred arrangements the outlet port is provided by a separate outlet member which is mounted so as to close an opening in the liquid reservoir. This is advantageous since it allows the liquid reservoir and outlet member to be made from different materials each of which can be optimised for its function. For example, the dimensions of the liquid reservoir may be relatively uncritical and so it could be made relatively inexpensively, e.g. as an injection moulded plastics component. On the other hand, the dimensions of the outlet port of the outlet member are likely to be more critical and it might for example by made to a tighter tolerance, e.g. from metal.

As above, the outlet member and liquid reservoir preferably together form a cartridge, and in preferred embodiments a cassette comprising a plurality of such cartridges is provided. Thus when viewed from a further aspect the present invention provides a cassette comprising a plurality of cartridges for dispensing liquid therefrom, each cartridge comprising a liquid reservoir and an outlet member mounted so as to close an opening in the liquid reservoir, said outlet member providing an outlet port through which said liquid can be forced by a pulse of pressurised gas.

Preferably at least the liquid reservoirs of said cartridges are formed integrally with one another to form said cassette.

In some preferred embodiments the outlet port comprises a protruding nozzle, e.g. a capillary tube. The bore of such a nozzle is preferably within the range 0.05 to 0.2 mm, most preferably about 0.1 mm. The length of the nozzle is preferably in the range 1 to 15 mm, most preferably 5 mm.

More preferably, the outlet port comprises an aperture in a wall of the liquid reservoir. The aperture is chosen in size to give the required volume of drop when a given pressure pulse is applied. The aperture however should be small enough that the surface tension in the liquid in the reservoir prevents it from leaking through.

In accordance with the first and second aspects of the invention, the wall of the liquid reservoir in which the aperture is provided may be integral with the reservoir but preferably it is a separate wall member mounted so as to close an opening in the liquid reservoir.

Where, as is preferred, a plurality of cartridges together form a cassette, each may have its own such wall member or two or more of the cartridges may share a wall member with an aperture for each cartridge.

A single aperture may be provided for the or each liquid reservoir, or more may be provided to increase the volume that may be dispensed without increasing the size of the aperture (which could give rise to a greater probability of leaking).

The aperture could be any shape, but most conveniently it is round. However, it larger volumes of liquid are required an elongate slit could for example by employed.

In preferred embodiments the aperture is between 2 and 300 micrometers wide, preferably approximately 40 micrometers. If the aperture is a slit it could for example be 40×500 micrometers.

The wall member could be made from any suitable material, e.g. plastics, metal, glass or ceramics. Preferably it has the opposite relationship to water as the liquid for which it is intended to be used, i.e. preferably the member is hydrophilic if the liquid is hydrophobic and vice versa. It may have any suitable thickness, but preferably it is between 10 micrometers and 1000 micrometers (1 mm), most preferably approximately 50 micrometers.

The aperture may be formed by suitably precise technique e.g. etching, electroplating, laser drilling or mechanical drilling.

The wall member may be fixed to the or each liquid reservoir in any suitable manner e.g. gluing, ultrasonic welding, friction welding etc. In one preferred embodiment the liquid reservoir tapers towards its open end and the wall member is pressed into an interference fit with the tapered end. The wall member therefore preferably has the same peripheral shape as the liquid reservoir, most preferably this being round. The diameter of the wall member in such a case is preferably between 0.5 and 6 mm, most preferably approximately 2 mm.

The cartridge or each cartridge of a cassette may be filled with a suitable liquid prior to use, e.g. a lyophilised reagent which is dissolved in water when required. The preferred embodiments of the invention in which the liquid reservoir is adjacent the outlet port are advantageous in this context since just the required amount of reagent can be made up as required without extra being required to accommodate dead space in pipes etc.

Cassettes of cartridges in accordance with the invention as described above are useful in many applications including but not limited to immuno assays, cell assay, drug screening and they are particularly useful for sequencing DNA using the method often referred to as "Sequencing By Synthesis" as they allow for example a cassette having cartridges containing each of the four nucleotides required for DNA sequencing. Preferably therefore the cartridges respectively contain one or more nucleotides. The ability to provide a plurality of cartridges in a single cassette further allows a complete set of reagents required for a sequencing programme to be provided. Thus preferably further cartridges of the cassette respectively contain one or more enzymes, more preferably selected from a group comprising polymerase, luciferase, adenosine triphosphate (ATP) sulfurylase, and a nucleotide-degrading enzyme such as apyrase. Such a set of reagents is particularly useful for the method of genetic sequencing set out in WO 98/13523. Indeed it will be appreciated that the invention extends to a method of genetic sequencing using a liquid dispensing apparatus or cassette as herein described.

As discussed above, cartridges of the kind described above may be filled by a user with the appropriate liquid as required. Alternatively the cartridge or each cartridge of a cassette is pre-filled with the appropriate liquid and sealed, the seal being broken upon mounting the cartridge into an apparatus which includes the gas pulse generation means. Preferably the seal is broken by the action of mounting the cartridge into the apparatus. Advantageously a conduit for establishing gaseous communication with the interior of the liquid reservoir of the cartridge breaks the seal.

It will be seen from the above that a sealed cartridge containing a liquid to be dispensed by means of apparatus in accordance with the first aspect of the invention is in itself not only novel, but particularly convenient for a user and thus when viewed from a further aspect the present invention provides a cartridge comprising a liquid reservoir having a predetermined liquid received therein, said reservoir being closed at one end thereof by frangible sealing means, and an outlet port attached to or integrally formed with said reservoir and in fluid communication therewith.

As an alternative it will be seen that the invention extends to a cartridge for use in a liquid dispensing apparatus as hereinbefore described comprising a liquid reservoir, and an outlet port attached to or integrally formed with said reservoir and in fluid communication therewith, in combination with a reagent, preferably a nucleotide or enzyme.

The reagent e.g. nucleotide or enzyme could be in a suitable liquid form or could be lyophilised. In the latter case a readily available diluent such as water could be used, or a suitable diluent could instead also be provided as part of the combination.

The frangible sealing means preferably comprises a foil membrane e.g. of aluminium covering an opening onto the reservoir. This is a cost-effective way of retaining liquid in the reservoir without it becoming contaminated, whilst at the same time being relatively easy to pierce—e.g. by a gas nozzle associated with the gas pulse generation means.

The predetermined liquid preferably comprises a nucleotide or an enzyme.

Where an enzyme is provided, either as the predetermined liquid in a pre-filled cartridge or as a separate reagent to be added by a user, the enzyme is preferably selected from a group comprising polymerase, luciferase, adenosine triphosphate (ATP) sulfurylase, and a nucleotide-degrading enzyme such as apyrase.

The means for generating the gas pulses may comprise any suitable means—e.g. a bellows arranged to undergo a rapid reduction in volume. Preferably however the pulse generation means comprises a source of pressurised gas which may be selectively placed into communication with the liquid reservoir. Such arrangements are especially beneficial since a single source of pressurised gas may be used to drive a plurality of liquid reservoirs, thereby giving a significant saying in cost over arrangements where driving means are individually provided for each of a number of nozzles. Means for selectively placing the liquid reservoir into communication with the source of gas may be provided for each of such liquid reservoirs or two or more of them may be associated with a single selection means so that their contents are dispensed simultaneously.

Preferably one or more valves is provided to effect said selective communication and in the preferred embodiment an electromagnetic valve is used. This is particularly advantageous since electromagnetic valves can be operated very quickly and accurately with little mechanical wear.

Where, as is preferred, the apparatus for dispensing liquid comprises gas pulse generation means in the form of means for selectively communicating a source of pressurised gas with the liquid reservoir, the source of pressurised gas may be comprised within the apparatus. Most preferably the source of pressurised gas comprises a compressor supplying a pressure reservoir. Alternatively, the apparatus may comprise a gas inlet for connection to an external source of pressurised gas. In either case the apparatus of the invention preferably comprises means to regulate the pressure of the incoming gas thereby allowing the amplitude of the pulses generated to be accurately controlled and thus the volume of liquid to be accurately controlled as a consequence. The pressure regulation means may comprise a mechanical release valve or the like. Preferably however such means comprises an electronic pressure sensor which is used to monitor the pressure in the reservoir or gas inlet and means for increasing or decreasing said pressure in response to the signal from the pressure sensor to maintain the pressure within a predetermined range.

The gas pulse generation means preferably generates pressure pulses having an amplitude in the range 200 to 1000 millibars, with a pulse width in the range 1-1000 milliseconds. This enables volumes in the range 50 nl 10000 nl (10 µl) to be dispensed.

Certain preferred embodiments of the present invention will now be described, by way of example only, with reference to the accompanying drawings.

Turning to FIG. 1 there may be seen a liquid dispensing apparatus comprising a cartridge cassette designated generally by the reference numeral 1. This cassette contains eight cartridges 2, three of which are visible in the drawing. Each cartridge 2 is partly filled with a reagent 4 used for genetic sequencing. The volume of the cartridges is approximately 2 ml. Different reagents 4 are provided in each cartridge 2. Specifically, four of the cartridges 2 contain the deoxynucleotide triphosphate of one each of the four bases cytosine, guanine, adenosine and thymine. Four further cartridges 2 contain polymerase, luciferase, apyrase and ATP sulfurylase. Equally however some of all of the cartridges could have the same contents.

At the end of each cartridge 2 there is a capillary nozzle 6. This nozzle has a bore of 0.1 mm. In the depicted embodiment the nozzle 6 is integrally moulded with the rest of the cartridge 2 from a polymer. However the cartridge could be formed with means to receive a separate nozzle.

The cassette 1 has an outer case 8 which protects the cartridges 2 from contamination by the user handling them and conversely protects the user from having to come into contact with the liquid being dispensed or the very fine, i.e. sharp nozzles 6. Apertures 10 are provided in the base of the cassette casing 8 which are aligned with the nozzles 6 to allow the liquid through.

At the upper end of the cassette 1 a thin metal foil 16 is provided over the tops of the cartridges 2 to seal them. The foil 16 extends across the open upper end of the cassette 1 formed by the side walls of the casing 8, but slightly downwardly set from the top edge so as to leave on upstanding lip around the top of the foil 16.

The cassette 1 is installed in a carriage 18 which can be moved laterally in both directions over a Micro Titre Plate (MTP) 12. The MTP has 96 wells 14, three of which are shown. The cassette 1 is actually received in a downwardly tapering chamber 20, so as to rest on an apertured plate 22, the apertures of which are in alignment with the apertures 10 in the cassette and, when the carriage 18 is properly positioned, also with the wells 14 of the MTP 12.

The cassette 1 is retained in the chamber 20 by means of a hinged lid 3, having a rubber seal 24 on its underside which is a tight fit inside the lip at the top edge of cassette casing 8. The seal 24 is arranged also to ensure that the cartridges 2 are sealed with respect to one another as well as with respect to the lid 3.

Mounted in the lid 3 is an array of punching cannulae 28, one for each of the cartridges 2. These cannulae 28 have sharp tips and so as the lid 3 is hinged downwardly onto the cassette 1 in the chamber 20, the cannulae 28 pierce the foil seal 16. The other ends of the cannulae are each connected by means of a pipe 26 to a source of pressurised gas for a predetermined time to produce a pulse of gas. The pressurised gas is generated by a compressor type EC Genius/M 202 2305 EU.SV.C which is commercially available from Fini, Zola, Predosa, Bo—Italy.

The pulse of gas forces a measured amount of reagent 4 out of the cartridge 2, through the nozzle 6 and into the corresponding well 14 on the MTP 12. A 500 millibar pulse, for 10 milliseconds dispenses approximately 200 nanoliters of reagent into the well 14. Reagent is only dispensed from one of the cartridges 2 at a time although simultaneous dispensing is also possible and this could be useful e.g. where a plate having a greater number of wells was used with an interleaved series of wells used so that dispensing into the wells of several distinct series can be carried out without moving the carriage 18.

Once the reagents in the cartridges have been used, the cassette may simply be removed by opening the lid 3 and replaced with a new one, the fresh seals being broken by the cannulae 28. Since neither the cannulae 28 nor any other permanent part of the apparatus comes into contact with the reagents at any stage, there is little chance of contamination and it is not necessary to clean the apparatus between uses, even if different reagents are being used.

Figure 2:
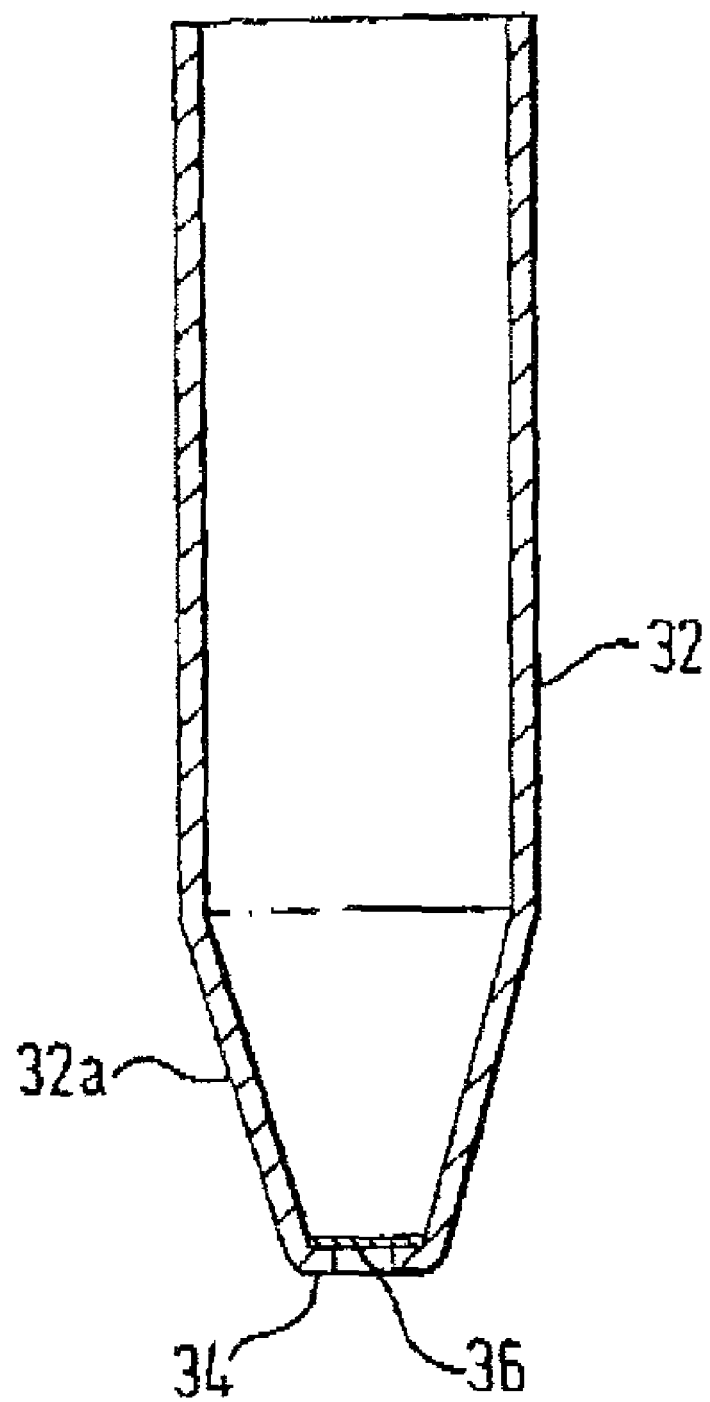
FIG. 2 is a cross-section through a cartridge in accordance with a second embodiment of the invention.

FIG. 2 shows part of the cartridge 30 of another embodiment of the invention. It will be seen that the liquid reservoir 32 tapers at its lower end 32a to form an opening circumscribed by an annular lip 34. The reservoir 32 and lip 34 are integrally formed in injection moulded plastics. The bottom opening is closed by a thin metallic foil disc 36 which has a central aperture drilled into it. The disc 36 is pressed into the end of the liquid reservoir 32 thereby forming a fluid-tight interference fit. The disc is 2 mm in diameter and 50 micrometers thick. The aperture is essentially circular with a diameter of approximately 40 micrometers. This is sufficiently small to prevent any leakage of liquid from the reservoir 32.

This embodiment operates in exactly the same way as the embodiment already described, although it will be appreciated that it has the additional benefits that the size of the aperture is easier to control precisely than is the bore of the capillary tube, and furthermore there is no potentially hazardous sharp tip.

Although embodiments of the invention having a cassette comprising several cartridges have been described, it will be understood by those skilled in the art that the invention is not limited to using several cartridges and that a single cartridge reservoir could be used instead. Furthermore, the liquid reservoir need not be removable and could instead be an integral part of the apparatus.

The invention claimed is:

1. A cassette comprising a plurality of cartridges for dispensing liquid drops in the range of 10-500 nanoliters therefrom, each cartridge comprising a liquid reservoir and an outlet member attached and adjacent to the liquid reservoir, said outlet member comprising an aperture, and wherein the liquid reservoir contains a quantity of liquid and is closed at one end thereof by a frangible sealing means.

2. The cassette as claimed in claim 1 wherein at least the liquid reservoirs of said cartridges are a unitary structure.

3. The cassette as claimed in claim 2 wherein said outlet member comprises a single aperture.

4. The cassette as claimed in claim 1 wherein said aperture has a width of between 2 and 300 micrometers.

5. The cassette as claimed in claim 1 wherein said frangible sealing means comprises a foil membrane.

6. The cassette as claimed in claim 1 wherein said liquid reservoir contains a nucleotide or enzyme.

7. The cassette as claimed in claim 6 wherein said liquid reservoir contains an enzyme selected from a group comprising polymerase, luciferase, adenosine triphosphate (ATP) sulfurylase, and a nucleotide-degrading enzyme such as apyrase.

8. A liquid dispensing apparatus comprising a cassette as claimed in claim 1 and a pressurised gas source.

9. A cassette comprising a plurality of cartridges for dispensing liquid drops in the range of 10-500 nanoliters therefrom, each cartridge comprising a liquid reservoir and a protruding nozzle attached and adjacent to the liquid reservoir wherein each liquid reservoir contains a quantity of liquid and is closed at one end thereof by a frangible sealing means.

10. The cassette as claimed in claim 9 wherein said frangible sealing means comprises a foil membrane.

11. The cassette as claimed in claim 9 wherein said liquid reservoir contains a nucleotide or enzyme.

12. The cassette as claimed in claim 11 wherein said liquid reservoir contains an enzyme selected from a group comprising polymerase, luciferase, adenosine triphosphate (ATP) sulfurylase, and a nucleotide-degrading enzyme such as apyrase.

13. A cassette comprising a plurality of cartridges for dispensing liquid drops in the range 10-500 nanoliters therefrom, each cartridge comprising a liquid reservoir and a protruding nozzle attached and adjacent to the liquid reservoir wherein said protruding nozzle further comprises a disc with a central aperture.

14. The liquid dispensing apparatus including a cassette or cartridge as claimed in claim 13 and a pressurised gas source.

15. The cassette as claimed in claim 13 wherein said protruding nozzle is a capillary tube.

* * * * *